United States Patent
Parsons et al.

(10) Patent No.: US 6,492,415 B2
(45) Date of Patent: Dec. 10, 2002

(54) USE OF BENZOPYRANOLS TO TREAT NEUROLOGICAL DISORDERS

(75) Inventors: Andrew Parsons, Arlesey (GB); Mervyn Thompson, Harlow (GB); Neil Upton, Harlow (GB); John Morris Evans, Roydon (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/909,215

(22) Filed: Jul. 19, 2001

(65) Prior Publication Data

US 2002/0010209 A1 Jan. 24, 2002

Related U.S. Application Data

(63) Continuation of application No. 09/242,799, filed as application No. PCT/EP97/05168 on Sep. 15, 1997, now abandoned.

(30) Foreign Application Priority Data

Sep. 18, 1996 (GB) .............................................. 9619492

(51) Int. Cl.$^7$ ............................................. A61K 31/353
(52) U.S. Cl. ........................ 514/456; 514/454; 514/455
(58) Field of Search ................................ 514/456, 454, 514/455

(56) References Cited

FOREIGN PATENT DOCUMENTS

| WO | 95/34545 | * 12/1995 |
|---|---|---|
| WO | WO 95/34546 A | 12/1995 |

* cited by examiner

*Primary Examiner*—Phyllis G. Spivack
(74) *Attorney, Agent, or Firm*—Linda E. Hall; Stephen Venetianer; Charles M. Kinzig

(57) ABSTRACT

Benzopyran derivatives and analogs are disclosed as useful for the treatment and/or prophylaxis of neuralgia, trigeminal neuralgia, neuropathic pain, dental pain and cancer pain.

9 Claims, No Drawings

USE OF BENZOPYRANOLS TO TREAT NEUROLOGICAL DISORDERS

This application is a continuation of application Ser. No. 09/242,799, filed Feb. 23, 1999, now abandoned, which is a 371 of PCT/EP97/05168, filed Sep. 15, 1997.

This invention relates to a novel method of treatment.

EP-A-0 126 311 discloses substituted benzopyran compounds having blood pressure lowering activity, including 6-acetyl-trans-4-(4-fluorobenzoylamino)-3,4-dihydro-2,2-dimethyl-2H-1-benzopyran-3-ol.

Also EP-A-0 376 524, EP-A-0 205 292, EP-A-0 250 077, EP-A-0 093 535, EP-A-0 150 202, EP-A-0 076 075 and WO/89/05808 (Beecham Group plc) describe certain benzopyran derivatives which possess anti-hypertensive activity.

EP-A-0 350 805 (Biersdorf), EP-A-0 277 611, EP-A-0 277 612, EP-A-0 337 179 and EP-A-0 355 565 (Hoechst Aktiengesellschaft); EP-A-0 466 131 (Nissan Chemical Industries Ltd), EP-A-0 339 562 (Yoshitomi Pharmaceuticals), EP-A-0 415 065 (E. Merck), EP-A-0 450 415 (Squibb), EP-A-0 482 934, EP-A-0 296 975, JO-2004-791 and WO89/07103 also describe certain benzopyran derivatives which are believed to possess anti-hypertensive activity.

EP-A-0 430 621 and EP-A-0 385 584 (Beecham Group plc) describe the resolution of certain intermediates useful in the preparation of the compounds described in the above mentioned patent applications.

EP-A-0 139 992 (Beecham Group plc) describes certain benzopyran derivatives which have cis isomerism at position 3 and 4 which compounds are described as possessing anti-hypertensive activity.

EP-A-0 587 645, EP-A-0 673 373, EP-A-0 673 374, EP-A-0 673 248, EP-A-0 674 519, WO95/34545, WO95/34547 and WO95/34546 (SmithKline Beecham plc) describe groups of compounds possessing inter alia anti-convulsant activity, and which are also believed to have utility in the treatment or prevention of mania, depression and the effects associated with withdrawal from substances of abuse.

It has now been surprisingly found that compounds from the above groups have additional activity and are believed to have utility in the treatment and/or prophylaxis of degenerative diseases such as Huntingdon's chorea, schizophrenia, neurological deficits associated with AIDS, sleep disorders (including circadian rhythm disorders, insomnia and narcolepsy), tics (e.g., Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity) and temporomandibular joint dysfunction.

Accordingly, the present invention provides a method of treatment and/or prophylaxis of degenerative diseases such as Huntingdon's chorea, schizophrenia, neurological deficits associated with AIDS, sleep disorders (including circadian rhythm disorders, insomnia and narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, MS and motor neurone disease, ataxias, muscular rigidity (spasticity), temporomandibular joint dysfunction, which comprises administering to the sufferer in need thereof an effective or prophylactic amount of a compound of formula (A) or pharmaceutically acceptable salt or solvate thereof:

(A)

wherein:

P is a ring system selected from the following:

a)

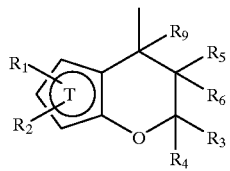

wherein;

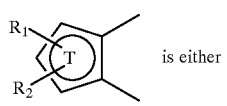 is either i)

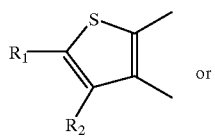

or ii)

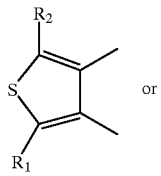

or iii)

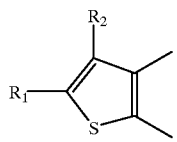

and the other variables are as defined below:

b)

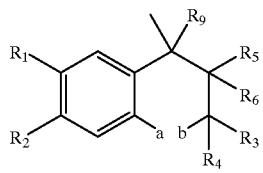

in which either a and b together represent a bond or $CH_2$ or a and b together represent a carbonyl group, a group $C=NOR^F$, $CHOR^F$ or

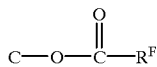

where $R^F$ is hydrogen or $C_{1-6}$ alkyl; or c)

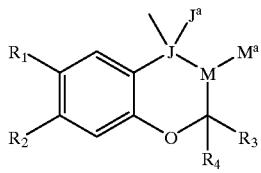

in which either J is nitrogen and $J^a$ is a lone pair of electrons, M is carbon and $M^a$ is $R_5$; or J is carbon and M is nitrogen and $J^a$ and $M^a$ are hydrogen; or d)

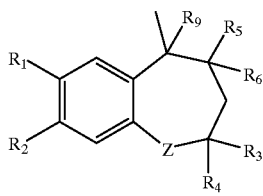

in which Z is oxygen or $CH_2$;

(e)

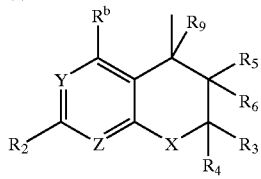

wherein: 4
either Y is N and $R_2$ is hydrogen, or Y is C—$R_1$; where:
either one of $R_1$ and $R_2$ is hydrogen and the other is selected from the class of hydrogen, $C_{3-8}$ cycloalkyl, $C_{1-6}$ alkyl optionally interrupted by oxygen or substituted by hydroxy, $C_{1-6}$ alkoxy or substituted aminocarbonyl, $C_{1-6}$ alkylcarbonyl, $C_{1-6}$ alkoxycarbonyl, $C_{1-6}$ alkylcarbonyloxy, $C_{1-6}$ alkoxy, nitro, cyano, halo, trifluoromethyl, $CF_3S$, or a group $CF_3$—A—, where A is —$CF_2$—, —CO—, —$CH_2$—, CH(OH), $SO_2$, SO, $CH_2$—O, or CONH, or a group $CF_2H$—A'— where A' is oxygen, sulfur, SO, $SO_2$, $CF_2$ or CFH; trifluoromethoxy, $C_{1-6}$ alkylsulfinyl, perfluoro $C_{2-6}$ alkylsulfonyl, $C_{1-6}$ alkylsulfonyl, $C_{1-6}$ alkoxysulfinyl, $C_{1-6}$ alkoxysulfonyl, aryl, heteroaryl, arylcarbonyl, heteroarylcarbonyl, phosphono, arylcarbonyloxy, heteroarylcarbonyloxy, arylsulfinyl, heteroarylsulfinyl, arylsulfonyl, heteroarylsulfonyl in which any aromatic moiety is optionally substituted, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulfinyl, aminosulfonyl or aminocarbonyl, any amino moiety being optionally substituted by one or two $C_{1-6}$ alkyl groups, or $C_{1-6}$ alkylsulfinylamino, $C_{1-6}$ alkylsulfonylamino, $C_{1-6}$ alkoxysulfinylamino or $C_{1-6}$ alkoxysulfonylamino, or ethylenyl terminally substituted by $C_{1-6}$ alkylcarbonyl, nitro or cyano, or —$C(C_{1-6}$ alkyl)NOH or —$C(C_{1-6}$ alkyl)$NNH_2$, or one of $R_1$ and $R_2$ is nitro, cyano or $C_{1-3}$ alkylcarbonyl and the other is halo, $C_{1-4}$ alkyl, methoxy or amino optionally substituted by one or two $C_{1-6}$ alkyl or by $C_{2-7}$ alkanoyl;

or $R_1$ and $R_2$ together are —$(CH_2)_4$—; $(CH_2)_x CO(CH_2)_y$ where x is 0 to 3 and y is 0 to 3 with the proviso that x+y is at least 2x; or —CH=CH—CH=CH—; or form an optionally substituted triazole or oxadiazole ring, or together form a group $CONR^cCO$ where $R^c$ is hydrogen, $C_{1-6}$ alkyl, aralkyl or heteroarylalkyl;

Z is N only when Y is C—$R_1$ or Z is C—$R^a$ when Y is N or C—$R_1$; wherein $R^a$ is hydrogen, halogen, nitro; $C_{1-4}$ alkylcarbonyl, $C_{1-4}$ alkyl; aryl $C_{1-4}$ alkyl, aryl $C_{1-4}$ alkenyl, heteroaryl $C_{1-4}$ alkyl or heteroaryl $C_{1-4}$ alkenyl, $R^b$ is hydrogen, halogen, nitro; $C_{1-4}$ alkylcarbonyl or $C_{1-4}$ alkyl; and in which any aryl or heteroaryl or alkyl moiety associated with $R^a$ or $R^b$ are optionally substituted;

one of $R_3$ and $R_4$ is hydrogen or $C_{1-4}$ alkyl and the other is $C_{1-4}$ alkyl, $CF_3$ or $CH_2X^a$ where $X^a$ is fluoro, chloro, bromo, iodo, $C_{1-4}$ alkoxy, hydroxy, $C_{1-4}$ alkylcarbonyloxy, —S—$C_{1-4}$ alkyl, nitro, amino optionally substituted by one or two $C_{1-4}$ alkyl groups; cyano or $C_{1-4}$ alkoxycarbonyl or $R_3$ and $R_4$ together are $C_{2-5}$ polymethylene optionally substituted by $C_{1-4}$ alkyl;

$R_5$ is $C_{1-6}$ alkylcarbonyloxy, benzoyloxy, $ONO_2$, benzyloxy, phenyloxy or $C_{1-6}$ alkoxy and $R_6$ and $R_9$ are hydrogen or $R_5$ is hydroxy and $R_6$ and $R_9$ are independently hydrogen or $C_{1-2}$ alkyl;

$R^x$ is (a)

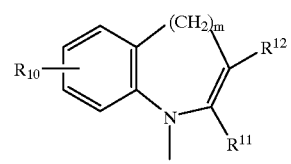

in which:
$R_{11}$ and $R_{12}$ are independently selected from hydrogen, alkyl, haloalkyl, cycloalkyl, aralkyl, cyano, nitro, $COR_{13}$, $CONHR_{13}$, $CONR_{13}R_{14}$ or halo where $R_{13}$ and $R_{14}$ are independently selected from hydrogen, alkyl, haloalkyl, aryl, aralkyl, cycloalkyl or (cycloalkyl)-alkyl;

$R_{10}$ is hydrogen, alkyl, haloalkyl, cycloalkyl, O—$R_{15}$, cyano, nitro, $CF_3$, halo, S-alkyl, $COR_{15}$, $COOR_{15}$, $NR_{15}CO$ alkyl or OCO alkyl where $R_{15}$ is hydrogen, alkyl, haloalkyl, aryl, aralkyl, cycloalkyl or (cycloalkyl)-alkyl; m is 0 or 1;

or (b) $R^x$ is a $R_8$—N—CO—$R_7$ group where
$R_7$ is heteroaryl or phenyl; both of which are optionally substituted one or more times independently with a group or atom selected from chloro, fluoro, bromo, iodo, nitro, amino optionally substituted once or twice by $C_{1-4}$ alkyl, cyano, azido, $C_{1-4}$ alkyl, $C_{1-4}$ alkoxy, trifluoromethoxy, trifluoromethyl; optionally substituted aryloxy or heteroaryloxy; $C_{1-4}$ alkoxy substituted by one or more halogens (excluding trifluoromethoxy); amino substituted by $C_{1-4}$ alkanoyl, aroyl aryl phenylsulfonyl or $C_{1-4}$ alkylsulfonyl; $C_{1-4}$ alkyl substituted by one or more halogens (excluding trifluoromethyl) or alkoxy; phenylsulfonyl $C_{1-4}$alkyl sulfonyl, aminosulfonyl in which the amino group is optionally substituted by $C_{1-4}$ alkyl; $CONH_2$ in which the amino group is optionally substituted by $C_{1-4}$ alkyl;

$R_8$ is hydrogen; $C_{1-6}$ alkyl, $OR_{1-6}$ or $NHCOR_{17}$ wherein $R_{16}$ is hydrogen, $C_{1-6}$ alkyl, formyl, $C_{1-6}$ alkanoyl, aroyl or aryl-$C_{1-6}$ alkyl and $R_{17}$ is hydrogen, $C_{1-6}$ alkyl, $C_{1-6}$ alkoxy, mono or di $C_{1-6}$ alkyl amino, amino, amino-$C_{1-6}$ alkyl, hydroxy-$C_{1-6}$ alkyl, halo-$C_{1-6}$ alkyl, $C_{1-6}$ acyloxy-$C_{1-6}$ alkyl, $C_{1-6}$ alkoxycarbonyl-$C_{1-6}$-alkyl, aryl or heteroaryl;

X is oxygen or $NR_{18}$ where $R_{18}$ is hydrogen or $C_{1-6}$ alkyl; and the $R^x$ group is cis or trans to the $R_5$ group.

Generally the cis compounds of formula (A) may be prepared from the corresponding trans compounds, procedures for the preparation of which are generally described in EP-0126311, EP-0376524, EP-205292, EP-0250077, EP-0093535, EP-0150202, EP-0076075, WO/89/05808, EP-0350805, EP-027761 1, EP-0277612, EP-0337179, EP-0339562, EP-0355565, EP-A-415 065 (E. Merck), EP-A-450 415 (Squibb) EP-0466131, EP-A-0482934, EP-A-0296975, JO-2004-791 and WO89/07103.

The cis compounds of formula (A) may be prepared by procedures generally described in or analogous to those described in EP-A-0139992.

The cis compounds of formula (A) may also be prepared according to the procedures described by G. Burrell et al, Tet. Letters, 31, 3649–3652 (1990) or by the procedures described by U. Quast and E. Villhauer, Eur. J. Pharmacol, Molecular Pharmacology Section 245, 165–171 (1993).

It should be appreciated that racemates for formula (A) may be resolved or enantiomerically purified compounds of formula (A) may be prepared using procedures conventional in the art and in particular using the procedures outlined in EP-0430631 and EP-0355584.

It should also be appreciated that it is preferred that the compounds of formula (A) may be prepared in the required enantiomeric form by forming a chirally pure epoxide using catalysts and conditions generally outlined in WO91/14694 or WO93/17026 and thereafter converting the epoxides to the required compound of formula (A) using procedures outlined herein.

The trans compounds of formula (A) may be prepared according to the procedures outlined in PCT/GB92/01045 which procedures are incorporated herein by reference or the trans compounds of formula (A) may be prepared according to methods analogous to these described in the one mentioned patents.

Reference is particularly directed to EP-A-0 587 645, EP-A-0 673 373, EP-A-0 673 374, EP-A-0 673 248, EP-A-0674 519, WO95/34545, WO95/34547 and WO95/34546 for compounds suitable for use in this invention.

Preferred compounds for use in this invention are trans-6-acetyl-4S-(4-fluorobenzoylamino)-3,4-dihydro-2,2-dimethyl-2H-1-benzopyran-3R-ol, hereinafter Compound 1 (for preparation see Example 20 of WO 92/22293) and cis-6-acetyl-4S-(3-chloro-4-fluorobenzoylamino)-3,4-dihydro-2,2-dimethyl-2H-1-benzopyran-3S-ol, hereinafter Compound 2 (for preparation see Example 17 of WO95/34545) and trans-6-acetyl-4S-(3,5-difluorobenzoylamino)-3,4-dihydro-2,2-dimethyl-2H-1-benzopyran-3R-ol, hereinafter Compound 3 (for preparation see Example 4 of WO95/34545).

The above compounds may be used in therapy as pharmaceutically acceptable salts, such as hydrochlorides, and pharmaceutically acceptable solvates, such as hydrates.

The administration to the mammal may be by way of oral, parenteral, sub-lingual or transdermal administration.

An amount effective to treat the disorders hereinbefore described depends on the usual factors such as the nature and severity of the disorders being treated and the weight of the mammal. However, a unit dose will normally contain 1 to 5000 mg, suitably 1 to 500 mg, for example an amount in the range of from 2 to 400 mg such as 2, 5, 10, 20, 30, 40, 50, 100, 200, 300 and 400 mg of the active compound. Unit doses will normally be administered once or more than once per day, for example 1, 2, 3, 4, 5 or 6 times a day, more usually 1 to 4 times a day, such that the total daily dose is normally in the range, for a 70 kg adult, of 1 to 5000 mg, for example 1 to 500 mg, that is in the range of approximately 0.01 to 15 mg/kg/day, more usually 0.1 to 6 mg/kg/day, for example 1 to 6 mg/kg/day.

It is greatly preferred that the compound of formula (I) is administered in the form of a unit-dose composition, such as a unit dose oral, including sub-lingual, rectal, topical or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulfate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, alumninium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surflctant or wetting agent is included in the composition to facilitate uniform distribution of the compound of the invention.

As is common practice, the compositions will usually be accompanied by written or printed directions for use in the medical treatment concerned.

The present invention further provides a pharmaceutical composition for use in the treatment and/or prophylaxis of degenerative diseases such as Huntingdon's chorea, schizophrenia, OCD, neurological deficits associated with AIDS, sleep disorders (including circadian rhythm disorders, insomnia and narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, MS and motor neurone disease, ataxias, muscular rigidity (spasticity) and temporomandibular joint dysfunction, which comprises a compound of formula (A), or a pharmaceutically acceptable salt or solvate thereof, and a pharmaceutically acceptable carrier.

In a further aspect the invention provides the use of a compound of formula (A), or a pharmaceutically acceptable salt or solvate thereof, for the manufacture of a medicament for the treatment and/or prophylaxis of degenerative diseases such as Huntingdon's chorea, schizophrenia, neurological deficits associated with AIDS, sleep disorders (including circadian rhythm disorders, insomnia and narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, MS and motor neurone disease, ataxias, muscular rigidity (spasticity) and temporomandibular joint dysfunction.

Such compositions and medicaments may be prepared in the manner as hereinbefore described.

This invention is particularly concerned with the treatment of neuropathic pain and trigeminal neuralgia, espesially by use of trans-6-acetyl-4S-(4-fluorobenzoylamino)-3,4-dihydro-2,2-dimethyl-2H-1-benzopyran-3R-ol (Compound 1) and cis-6-acetyl-4S-(3-chloro-4-fluorobenzoylamino)-3,4-dihydro-2,2-dimethyl-2H-1-benzopyran-3S-ol (Compound 2) and trans-6-acetyl-4S-(3,5-difluorobenzoylamino)-3,4-dihydro-2,2-dimethyl-2H-1-benzopyran 3R-ol (Compound 3).

The present invention is illustrated by the following pharmocological data:

Trigeminal nerve model in anaesthetised cats

Cats were anaesthetised with α-chloralose (90–110 mg/kg i.v.) and artificially respired with room air. Body temperature was maintained at 37–38 C. A femoral artery was cannulated for recording of blood pressure and heart rate. Arterial blood flow was recorded by a Doppler flow probe placed around the right common carotid artery. Bipolar stainless electrodes were stereotaxically placed into each trigeminal ganglion.

Guanethidine (3 mg/kg i.v.) was then administered and 45 min allowed for stabilisation. Stimulation (2 mA, 10 Hz for 2 min) of the trigeminal ganglion, ipsilateral to the carotid artery from which blood flow was measured, increased blood flow and reduced carotid vascular resistance. The ability of drugs, given i.v. to modulate this response was used to assess their effects on the trigemino-vascular system.

Intravenous administration of Compound 1 (n=3) or Compound 2 (n=4) at a rate of 3.4 μmol/h produced a significant inhibition of TGN-induced reduction in carotid vascular resistance at 4 hours (Table 1).

Intraduodenal administration of Compound I (n=3) or Compound 2 (10 mg.kg) also produced significant inhibition of TGN-induced reduction in carotid vascular resistance (Table 2) after 3 hours.

TABLE 1

Effects of continuous intravenous administration Compound 1 and Compound 2 on TGN-induced reduction in carotid vascular resistance in the anaesthetised cat

| | n | % Change in TGN-reduction in carotid vascular resistance at 4 hours following continuous iv infusion (mean ± sem) |
|---|---|---|
| control (3.4 μmol/h) | 4 | 11.6 ± 8.6 |
| control (11 μmol/h) | 3 | 15.7 ± 10 |
| Compound 1 3.4 μmol/h | 3 | −29.1 ± 3.7* |
| Compound 2 3.4 μmol/h | 4 | −30.0 ± 6.6* |
| Compound 2 11 μmol/h | 4 | −21.8 ± 14* |

*$P < 0.05$

TABLE 2

Effects of intraduodenal administration of Compound 1 or 2 (10 mg/kg) on TGN-induced administration in the anaethetised cat

| | n | % Changes of TGW-induced reduction in carotid vascular resistance 3 hours (mean ± sem) |
|---|---|---|
| control (labrosol) | 3 | 30.6 ± 12.2 |
| Compound 1 (labrasol) | 3 | −43 ± 12.9* |
| control (methylcellulose) | 2 | 6.8 |
| Compound 2 (methylcellulose) | 2 | −69 |

Compound 3 had marked effects on TGN stimulation-induced reductions in carotid vascular resistance in the guanethidine treated anaesthetised cat. In the absence of drug treatment, TGN stimulation typically produced an approximate 40–50% reduction in carotid vascular resistance which was reproducible at 30 minute intervals. At 2 hours post administration, intraduodenal bolus administration of Compound 3 (10 mg/kg) produced a 77% (n=4) inhibition of trigeminal nerve mediated responses, whereas no inhibition was observed in vehicle treated animals (−4.1%, n=3).

Neuropathic Pain Model in Anesthetised Rats.

The left sciatic nerve was exposed in anaesthetised rats and dorsal 50–60% of the nerve ligated as described by Seltzer et al 1990 (Pain 43, p205–218). The surgical wound was then closed and the animals allowed to recover. Thermal nociception was measured by latency to withdraw hind paw from an infrared light source pre-surgery (8 days and 1 day before surgery) and at regular intervals following nerve ligation.

Compounds were administered as a single or repeat dose on established hyperalgesia, typically 14 days post ligation. Compounds were administered as either an oral or systemic formulation and the change in thermal nociception recorded for up to 40 days.

What is claimed is:

1. A method of treatment of neuralgia, trigeminal neuralgia, neuropathic pain, dental pain, and cancer pain, which comprises administering to the sufferer in need thereof an effective or prophylactic amount of a compound of formula (A) or pharmaceutically acceptable salt or solvate thereof:

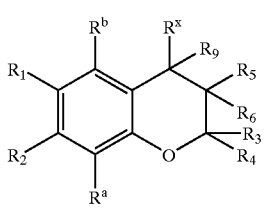

(A)

wherein:
either one of $R_1$ and $R_2$ is hydrogen and the other is selected from the class of hydrogen, $C_{3-8}$ cycloalkyl, $C_{1-6}$ alkyl optionally interrupted by oxygen or substituted by hydroxy, $C_{1-6}$ alkoxy or substituted aminocarbonyl, $C_{1-6}$ alkylcarbonyl, $C_{1-6}$ alkoxycarbonyl, $C_{1-6}$ alkylcarbonyloxy, $C_{1-6}$ alkoxy, nitro, cyano, halo, trifluoromethyl, $CF_3S$, or a group $CF_3$—A—, where A is —$CF_2$—, —CO—, —$CH_2$—, CH(OH), $SO_2$, SO, $CH_2$—O, or CONH, or a group $CF_2H$—A'— where A' is oxygen, sulfur, SO, $SO_2$, $CF_2$ or CFH; trifluoromethoxy, $C_{1-6}$ alkylsulfinyl, perfluoro $C_{2-6}$ alkylsulfonyl, $C_{1-6}$ alkylsulfonyl, $C_{1-6}$ alkoxysulfinyl, $C_{1-6}$ alkoxysulfonyl, aryl, arylcarbonyl, phosphono, arylcarbonyloxy, arylsulfinyl, arylsulfonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulfinyl, aminosulfonyl or aminocarbonyl, any amino moiety being optionally substituted by one or two $C_{1-6}$ alkyl groups, or $C_{1-6}$ alkylsulfinylamino, $C_{1-6}$ alkylsulfonylamino, $C_{1-6}$ alkoxysulfinylamino or $C_{1-6}$ alkoxysulfonylamino, or ethylenyl terminally substituted by $C_{1-6}$ alkylcarbonyl, nitro or cyano, or —C($C_{1-6}$ alkyl)NOH or —C($C_{1-6}$alkyl)NNH$_2$, or one of $R_1$ and $R_2$ is nitro, cyano or $C_{1-3}$ alkylcarbonyl and the other is halo, $C_{1-4}$ alkyl, methoxy or amino optionally substituted by one or two $C_{1-6}$ alkyl or by $C_{2-7}$ alkanoyl;

or $R_1$ and $R_2$ together are —(CH$_2$)$_4$—; (CH$_2$)$_x$ CO(CH$_2$)$_y$ where x is 0 to 3 and y is 0 to 3 with the proviso that x+y is at least 2x; or —CH=CH—CH=CH—;

$R^a$ is hydrogen, halogen, nitro; $C_{1-4}$ alkylcarbonyl, $C_{1-4}$ alkyl; aryl $C_{1-4}$ alkyl or aryl $C_{1-4}$alkenyl, $R_b$ is hydrogen, halogen, nitro; $C_{1-4}$ alkylcarbonyl or $C_{1-4}$ alkyl; and in which any aryl or alkyl moiety associated with $R^a$ or $R^b$ is optionally substituted;

one of $R_3$ and $R_4$ is hydrogen or $C_{1-4}$ alkyl and the other is $C_{1-4}$ alkyl, $CF_3$ or $CH_2X^a$ where $X^a$ is fluoro, chloro, bromo, iodo, $C_{1-4}$ alkoxy, hydroxy, $C_{1-4}$ alkylcarbonyloxy, —S—$C_{1-4}$ alkyl, nitro, amino optionally substituted by one or two $C_{1-4}$ alkyl groups; cyano or $C_{1-4}$ alkoxycarbonyl;

or $R_3$ and $R_4$ together are $C_{2-5}$ polymethylene optionally substituted by $C_{1-4}$ alkyl;

$R_5$ is $C_{1-6}$ alkylcarbonyloxy, benzoyloxy, ONO$_2$, benzyloxy, phenyloxy or $C_{1-6}$ alkoxy and $R_6$ and $R_9$ are hydrogen or $R_5$ is hydroxy and $R_6$ and $R_9$ are independently hydrogen or $C_{1-2}$ alkyl;

$R^x$ is a $R_8$—N—CO—$R_7$ group where $R_7$ is phenyl; which is optionally substituted one or more times independently with a group or atom selected from chloro, fluoro, bromo, iodo, nitro, amino optionally substituted once or twice by $C_{1-4}$ alkyl, cyano, azido, $C_{1-4}$ alkyl, $C_{1-4}$ alkoxy, trifluoromethoxy, trifluoromethyl; $C_{1-4}$ alkoxy substituted by one or more halogens, excluding trifluoromethoxy; amino substituted by $C_{1-4}$ alkanoyl, aroyl aryl phenylsulfonyl or $C_{1-4}$ alkylsulfonyl; $C_{1-4}$ alkyl substituted by one or more halogens, excluding trifluoromethyl, or alkoxy; phenylsulfonyl $C_{1-4}$ alkyl sulfonyl, aminosulfonyl in which the amino group is optionally substituted by $C_{1-4}$ alkyl; CONH$_2$ in which the amino group is optionally substituted by $C_{1-4}$ alkyl;

$R_8$ is hydrogen; $C_{1-6}$ alkyl, OR$_{16}$ or NHCOR$_{17}$, wherein $R_{16}$ is hydrogen, $C_{1-6}$ alkyl, formyl, $C_{1-6}$ alkanoyl, aroyl or aryl-$C_{1-6}$ alkyl and $R_{17}$ is hydrogen, $C_{1-6}$ alkyl, $C_{1-6}$ alkoxy, mono or di $C_{1-6}$ alkyl amino, amino, amino-$C_{1-6}$ alkyl, hydroxy-$C_{1-6}$ alkyl, halo-$C_{1-6}$ alkyl, $C_{1-6}$ acyloxy-$C_{1-6}$ alkyl, $C_{1-6}$ alkoxycarbonyl-$C_{1-6}$-alkyl or aryl; and the $R^x$ group is cis or trans to the $R_5$ group.

2. A method according to claim 1, for the treatment of trigeminal neuralgia.

3. A method according to claim 2 which the compound of formula (A) is trans-6-acetyl-4S-(4-fluorobenzoylamino)-3,4-dihydro-2,2-dimethyl- 2H-1-benzopyran-3R-ol or cis-6-acetyl-4S-(3-chloro-4-fluorobenzoylamino)- 3,4-dihydro-2,2-dimethyl-2H-1-benzopyran-3S-ol or trans-6-acetyl-4S-(3,5-difluorobenzoyl-amino)-3,4-dihydro-2,2-dimethyl-2H-1-benzopyran- 3R-ol, or a pharmaceutically acceptable salt or solvate thereof.

4. A method according to claim 1, for the treatment of neuropathic pain.

5. A method according to claim 4 in which the compound of formula (A) is trans-6-acetyl-4S-(4-fluorobenzoylamino)-3,4-dihydro-2,2-dimethyl- 2H-1-benzopyran-3R-ol or cis-6-acetyl-4S-(3-chloro-4-fluorobenzoylamino)- 3,4-dihydro-2,2-dimethyl-2H-1-benzopyran-3S-ol or trans-6-acetyl-4S-(3,5-difluorobenzoyl-amino)-3,4-dihydro-2,2-dimethyl-2H-1-benzopyran- 3R-ol, or a pharmaceutically acceptable salt or solvate thereof.

6. A method according to claim 1 in which the compound of formula (A) is trans-6-acetyl-4S-(4-fluorobenzoylamino)-3,4-dihydro-2,2-dimethyl- 2H-1-benzopyran-3R-ol or cis-6-acetyl-4S-(3-chloro-4-fluorobenzoylamino)-3,4-dihydro-2,2-dimethyl-2H-1-benzopyran-3S-ol or trans-6-acetyl-4S-(3,5-difluorobenzoyl-amino)-3,4-dihydro-2,2-dimethyl-2H-1-benzopyran-3R-ol, or a pharmaceutically acceptable salt or solvate thereof.

7. A method of treatment for the prophylaxis of neurological deficits associated with neuralgia, trigeminal neuralgia, neuropathic pain, dental pain, and cancer pain, which comprises administering to the sufferer in need thereof an effective or prophylactic amount of a compound of formula (A) or pharmaceutically acceptable salt or solvate thereof:

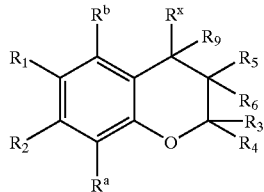

(A)

wherein:
either one of $R_1$ and $R_2$ is hydrogen and the other is selected from the class of hydrogen, $C_{3-8}$ cycloalkyl, $C_{1-6}$ alkyl optionally interrupted by oxygen or substituted by hydroxy, $C_{1-6}$ alkoxy or substituted aminocarbonyl, $C_{1-6}$ alkylcarbonyl, $C_{1-6}$ alkoxycarbonyl, $C_{1-6}$ alkylcarbonyloxy, $C_{1-6}$ alkoxy, nitro, cyano, halo, trifluoromethyl, $CF_3$ S, or a group $CF_3$—A—, where A is —$CF_2$—, —CO—, —$CH_2$—, CH(OH), $SO_2$, SO, $CH_2$—O, or CONH, or a group $CF_2H$—A'— where A' is oxygen, sulfur, SO, $SO_2$, $CF_2$ or CFH; trifluoromethoxy, $C_{1-6}$ alkylsulfinyl, perfluoro $C_{2-6}$ alkylsulfonyl, $C_{1-6}$ alkylsulfonyl, $C_{1-6}$ alkoxysulfinyl, $C_{1-6}$ alkoxysulfonyl, aryl, arylcarbonyl, phosphono, arylcarbonyloxy, arylsulfinyl, arylsulfonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulfinyl, aminosulfonyl or aminocarbonyl, any amino moiety being optionally substituted by one or two $C_{1-6}$ alkyl groups, or $C_{1-6}$ alkylsulfinylamino, $C_{1-6}$ alkylsulfonylamino, $C_{1-6}$ alkoxysulfinylamino or $C_{1-6}$ alkoxysulfonylamino, or ethylenyl terminally substituted by $C_{1-6}$ alkylcarbonyl, nitro or cyano, or —C($C_{1-6}$ alkyl)NOH or —C($C_{1-6}$ alkyl)NNH2,
or one of $R_1$ and $R_2$ is nitro, cyano or $C_{1-3}$ alkylcarbonyl and the other is halo, $C_{1-4}$ alkyl, methoxy or amino optionally substituted by one or two $C_{1-6}$ alkyl or by $C_{2-7}$ alkanoyl;
or $R_1$ and $R_2$ together are —$(CH_2)_4$—; $(CH_2)_x$ CO$(CH_2)_y$ where x is 0 to 3 and y is 0 to 3 with the proviso that x+y is at least 2x; or —CH=CH—CH=CH—;
$R^a$ is hydrogen, halogen, nitro; $C_{1-4}$ alkylcarbonyl or $C_{1-4}$ alkyl; alkyl or aryl $C_{1-4}$ alkenyl,
$R^b$ is hydrogen, halogen, nitro; $C_{1-4}$ alkylcarbonyl or $C_{1-4}$ alkyl; and in which any aryl or alkyl moiety associated with $R^a$ or $R^b$ is optionally substituted;
one of $R_3$ and $R_4$ is hydrogen or $C_{1-4}$ alkyl and the other is $C_{1-4}$ alkyl, $CF_3$ or $CH_2X^a$ where $X^a$ is fluoro, chloro, bromo, iodo, $C_{1-4}$ alkoxy, hydroxy, $C_{1-4}$ alkylcarbonyloxy, —S—$C_{1-4}$ alkyl, nitro, amino optionally substituted by one or two $C_{1-4}$ alkyl groups; cyano or $C_{1-4}$ alkoxycarbonyl;
or $R_3$ and $R_4$ together are $C_{2-5}$ polymethylene optionally substituted by $C_{1-4}$ alkyl;
$R_5$ is $C_{1-6}$ alkylcarbonyloxy, benzoyloxy, $ONO_2$, benzyloxy, phenyloxy or $C_{1-6}$ alkoxy and $R_6$ and $R_9$ are hydrogen or $R_5$ is hydroxy and $R_6$ and $R_9$ are independently hydrogen or $C_{1-2}$ alkyl;
$R^x$ is a $R_8$—N—CO—$R_7$ group where
$R_7$ is phenyl; both which is optionally substituted one or more times independently with a group or atom selected from chloro, fluoro, bromo, iodo, nitro, amino optionally substituted once or twice by $C_{1-4}$ alkyl, cyano, azido, $C_{1-4}$ alkyl, $C_{1-4}$ alkoxy, trifluoromethoxy, trifluoromethyl; $C_{1-4}$ alkoxy substituted by one or more halogens, excluding trifluoromethoxy; amino substituted by $C_{1-4}$ alkanoyl, aroyl aryl phenylsulfonyl or $C_{1-4}$ alkylsulfonyl; $C_{1-4}$ alkyl substituted by one or more halogens, excluding trifluoromethy, or alkoxy; phenylsulfonyl $C_{1-4}$ alkyl sulfonyl, aminosulfonyl in which the amino group is optionally substituted by $C_{1-4}$ alkyl; $CONH_2$ in which the amino group is optionally substituted by $C_{1-4}$ alkyl;
$R_8$ is hydrogen; $C_{1-6}$ alkyl, $OR_{16}$ or $NHCOR_{17}$, wherein $R_{16}$ is hydrogen, $C_{1-6}$ alkyl, formyl, $C_{1-6}$ alkanoyl, aroyl or aryl-$C_{1-6}$ alkyl and $R_{17}$ is hydrogen, $C_{1-6}$ alkyl, $C_{1-6}$ alkoxy, mono or di $C_{1-6}$ alkyl amino, amino, amino-$C_{1-6}$ alkyl, hydroxy-$C_{1-6}$ alkyl, halo-$C_{1-6}$ alkyl, $C_{1-6}$ acyloxy-$C_{1-6}$ alkyl, $C_{1-6}$ alkoxycarbonyl-$C_{1-6}$-alkyl or aryl; and
the $R^x$ group is cis or trans to the $R_5$ group.

8. A method of treatment for the prophylaxis of trigeminal neuralgia, using a compound chosen from the group consisting of trans-6-acetyl-4S-(4-fluorobenzoylamino)- 3,4-dihydro-2,2-dimethyl-2H-1-benzopyran-3R-ol or cis-6-acetyl- 4S-(3-chloro-4-fluorobenzoylamino)-3,4-dihydro-2, 2-dimethyl-2H-1-benzopyran- 3S-ol or trans-6-acetyl-4S-(3,5-difluorobenzoyl-amino)-3,4-dihydro- 2,2-dimethyl-2H-1-benzopyran-3R-ol , or a pharmaceutically acceptable solvate thereof.

9. A method of treatment for the prophylaxis of neuropathic pain, using a compound chosen from the group consisting of trans-6-acetyl-4S-(4-fluorobenzoylamino)- 3,4-dihydro-2,2-dimethyl-2H-1-benzopyran-3R-ol or cis-6-acetyl- 4S-(3-chloro-4-fluorobenzoylamino)-3,4-dihydro-2, 2-dimethyl-2H-1-benzopyran- 3S-ol or trans-6-acetyl-4S-(3,5-difluorobenzoyl-amino)-3,4-dihydro- 2,2-dimethyl-2H-1-benzopyran-3R-ol, or a pharmaceutically acceptable salt or solvate thereof.

* * * * *